United States Patent
Xie et al.

(10) Patent No.: US 9,512,420 B2
(45) Date of Patent: Dec. 6, 2016

(54) USE OF N-ACETYLNEURAMINIC ACID ALDOLASE IN CATALYTIC SYNTHESIS OF N-ACETYLNEURAMINIC ACID

(71) Applicant: Nanjing University of Technology, Nanjing (CN)

(72) Inventors: Jingjing Xie, Nanjing (CN); Wenyan Ji, Nanjing (CN); Hanjie Ying, Nanjing (CN); Wujin Sun, Nanjing (CN); Ting Guo, Nanjing (CN); Yong Chen, Nanjing (CN); Xiaochun Chen, Nanjing (CN); Jinglan Wu, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 63 days.

(21) Appl. No.: 14/396,317

(22) PCT Filed: Nov. 27, 2013

(86) PCT No.: PCT/CN2013/087987
§ 371 (c)(1),
(2) Date: Oct. 22, 2014

(87) PCT Pub. No.: WO2015/054947
PCT Pub. Date: Apr. 23, 2015

(65) Prior Publication Data
US 2016/0017308 A1    Jan. 21, 2016

(30) Foreign Application Priority Data

Oct. 16, 2013  (CN) .......................... 2013 1 0482695

(51) Int. Cl.
| | |
|---|---|
| C12N 9/00 | (2006.01) |
| C12N 9/88 | (2006.01) |
| C12P 19/26 | (2006.01) |
| C12N 15/63 | (2006.01) |

(52) U.S. Cl.
CPC ................ *C12N 9/88* (2013.01); *C12N 15/63* (2013.01); *C12P 19/26* (2013.01); *C12Y 401/03003* (2013.01); *Y02P 20/52* (2015.11)

(58) Field of Classification Search
None
See application file for complete search history.

(56) References Cited

PUBLICATIONS

Xu et al., "Efficient Whole-Cell Biocatalytic Synthesis of N-acetyl-D-neuraminic Acid", Adv. Synth. Catal. 349: 1614-1618 (2007).*
Kalinowski et al., "The complete Corynebacterium glutamicum ATCC 13032 genome sequence and its impact on the production of L-aspartate-derived amino acids and vitamins", Journal of Biotechnology 104: 5-25 (2003).*
Ji, W et al. Characterization of a novel N-acetylneuraminic acid lyase favoring N-acetylneuraminic acid synthesis. Scientific Repots. 5: 9341; 2015.

* cited by examiner

*Primary Examiner* — Anand Desai
(74) *Attorney, Agent, or Firm* — CBM Patent Consulting, LLC

(57) ABSTRACT

It discloses a use of N-acetylneuraminic acid aldolase with an amino acid sequence as shown in SEQ ID NO: 2 in catalytic synthesis of N-acetylneuraminic acid. The preparation of N-acetylneuraminic acid is to use the N-acetylneuraminic acid aldolase with the amino acid sequence as shown in SEQ ID NO: 2 as a catalyst, and N-acetylmannosamine and pyruvic acid as substrates.

5 Claims, 5 Drawing Sheets

US 9,512,420 B2

USE OF N-ACETYLNEURAMINIC ACID ALDOLASE IN CATALYTIC SYNTHESIS OF N-ACETYLNEURAMINIC ACID

This application is the U.S. national phase of International Application No. PCT/CN32013/087987 filed on 27 Nov. 2013 which designated the U.S. and claims priority to Chinese Application Nos. 201310482695.7 filed on 16 Oct. 2013, the entire contents of each of which are hereby incorporated by reference.

FIELD OF THE INVENTION

The present invention belongs to the field of biotechnology, and it relates to the use of N-acetylneuraminic acid aldolase (Nal), particularly relates to the use of Nal from *Corynebacterium glutamicum* ATCC 13032 in producing N-acetylneuraminic acid (Neu5Ac) by using N-acetylmannosamine (ManNAc) and pyruvic acid as the substrates.

BACKGROUND OF THE INVENTION

N-acetylneuraminic acid (N-acetyl-D-neuraminic acid, Neu5Ac) is an important milk powder additive, which can improve immunity of infants [1], meanwhile it can be used as a precursor for synthesizing anti-influenza A/B type virus drugs [2]. Synthesizing Neu5Ac by using ManNAc and pyruvic acid as the substrates under catalysis by Nal is the currently most primary synthesis route for Neu5Ac. Nal has been used in industrial synthesis of Neu5Ac [3-5], and synthesis of Neu5Ac from ManNAc and pyruvic acid under catalysis by Nal is a reversible reaction. Nal is widely distributed in the nature, and it is found in bacteria and mammals [6]. Many pathogenic bacteria, after invasion into human body, decompose human Neu5Ac by Nal as their carbon source and nitrogen source [6], thus currently there are a great number of reports on Nal from pathogenic bacteria. Besides Nal derived from pathogenic bacteria, there is also Nal found from food safe (generally regarded as safe, GRAS) strains, such as *Lactobacillus plantarum* WCFS1 [7] and *Taphylococcus carnosus* TM300 [8]. Because the substrate pyruvic acid is cheap [9] and Nals have relatively high temperature stability [10], it has been widely applied in the synthesis of Neu5Ac. However, currently all of Nal have a common defect: in a reversible catalytic synthesis reaction of Neu5Ac, the Nal is more prone to decompose Neu5Ac [7, 8, 11-14].

To obtain Nal of high activity and to resolve the issue of the chemical equilibrium of Nal being prone to decomposing Neu5Ac, this patent cloned and expressed N-acetylneuraminic acid aldolase (CgNal) from food safe strain *Corynebacterium glutamicum* ATCC 13032 [15]. It belongs to one of Nal family, comprising 312 amino acids, and its accession number in Genbank is NP_601846, its amino acid sequence is shown in SEQ ID NO: 2. The gene encoding this protein comprises 939 bp bases, its accession number in the Genbank is NC_003450.3, and its gene sequence is shown in SEQ ID NO:1. Reports on using CgNal in Neu5Ac synthesis has not been found until now.

SUMMARY OF THE INVENTION

The technical issue to be resolved by the present invention is to provide use of N-acetylneuraminic acid aldolase (Nal) in catalytic synthesis of N-acetylneuraminic acid (Neu5Ac) from N-acetylmannosamine (ManNAc) and pyruvic acid.

To resolve the above-described technical issue, a technical solution adopted by the present invention is as follow:

Use of N-acetylneuraminic acid aldolase (Nal) with an amino acid sequence as shown in SEQ ID NO: 2 in catalytic synthesis of N-acetylneuraminic acid (Neu5Ac) from N-acetylmannosamine (ManNAc) and pyruvic acid.

A specific method is synthesizing N-acetylneuraminic acid by using N-acetylneuraminic acid aldolase with the amino acid sequence as shown in SEQ ID NO: 2 as a catalyst, and using N-acetylmantosamine and pyruvic acid as substrates.

A more specific method is to express a recombinant strain comprising a gene sequence as shown in SEQ ID NO: 1, and a crude N-acetylneuraminic acid aldolase after lysis or a pure N-acetylneuraminic acid aldolase obtained by further nickel column purification is reacted with N-acetylmannosamine and pyruvic acid in a buffer, to obtain N-acetylneuraminic acid.

Wherein, said recombinant strain comprising the gene sequence as shown in SEQ ID NO: 1 is established by the following method: the gene of N-acetylneuraminic acid aldolase Nal is amplified by using *Corynebacterium glutamicum* ATCC13032 genome as a template and ligated to a pET-28a vector, then the recombinant plasmid is transformed into *E. coli* Rosetta (DE3).

Wherein, the method to express the recombinant strain comprising the gene sequence as showing in SEQ ID NO: 1 is: when the recombinant strain is incubated to $OD_{600}$=0.4 to 0.8, IPTG of final concentration 0.2 to 1.0 $mmol·L^{-1}$ is added at 15 to 37° C., and induced at 150 to 220 rpm for 4 to 12 hours. The preferred method is: when the recombinant strain is incubated to $OD_{600}$ of 0.6, IPTG of final concentration 0.2 $mmol·L^{-1}$ is added at 30° C., and induced at 220 rpm for 10 hours. Wherein, the condition of the nickel column purification is: a mixed protein is eluted with a 20 $mmol·L^{-1}$ imidazole solution, and the pure enzyme is eluted with a 500 $mmol·L^{-1}$ imidazole solution.

Wherein, the reaction ratio of N-acetylneuraminic acid aldolase with N-acetylglucosamine and pyruvic acid is: 0.36 to 300 $U·mL^{-1}$ crude enzyme or pure enzyme is reacted with 100 to 1000 $mmol·L^{-1}$ N-acetylmannosamine and 100 to 2000 $mmol·L^{-1}$ pyruvic acid.

Wherein, said buffer is 20 to 200 $mmol·L^{-1}$ Tris-HCl buffer of pH7 to 8.8 or 20 to 200 $mmol·L^{-1}$ glycine-NaOH buffer of pH 9.0 to 9.5, preferably Tris-HCl buffer of pH 7 to 8.5, most preferably Tris-HCl buffer of pH 7.5 or Tris-HCl buffer of pH 8.5.

Wherein, the reaction condition in the buffer is: the temperature being 25 to 60° C., and reaction time being 0.1 to 12 hours; preferably, the temperature being 35 to 45° C., and reaction time being 0.15 to 0.5 hours; most preferably, the temperature being 40° C., and reaction time being 0.15 to 0.5 hours.

The inventors, based on modern bioinformatics principle and in combination with molecular biotechnology, cloned the gene of N-acetylneuraminic acid aldolase from *Corynebacterium glutamicum* ATCC13032 by the method of genetic engineering and expressed it in *Escherichia coli*, and it was found be able to catalyze and synthesize Neu5Ac from ManNAc and pyruvate. Beneficial effects: the present invention firstly used the N-acetylneuraminic acid aldolase with the amino acid sequence as shown in SEQ ID NO: 2 in catalytic synthesis of Neu5Ac from ManNAc and pyruvate, and obtained very good effects, its enzyme activity was up to 12 U/mg. Because this reaction is a reversible reaction, compared with other Nals, the chemical equilibrium of this aldolase is more prone to a direction of N-acetylneuraminic acid synthesis i.e., sialic acid synthesis, meanwhile the expression effect of the enzyme is very good, no inclusion body is formed, and the expression amount of N-acetylneuraminic acid aldolase is large, being 5 folds of expression amount of aldolase gene derived from *Escherichia coli*, meanwhile *Corynebacterium glutamicum* is a food safe bacteria.

DETAILED DESCRIPTION OF THE EMBODIMENTS

The present invention can be better understood based on the following examples. However, one skilled in the field will easily understand that the specific material ratio described in the examples, process conditions and their results are used to illustrate the present invention only and should not be used to limit the invention described in detail in the claims.

Example 1

Establishing the Recombinant *E. coli* Rosseta (pET28a-CgNal)

1. Obtaining N-Acetylneuraminic Acid Aldolase Gene:

The genome of *Corynebacterium glutamicum* ATCC 13032 was extracted, then PCR was carried out by using the extracted genome as the template.

The primer adding enzyme digestion site used in expression vector was established, the sequence of the primer was as follow:

```
An upstream primer (CgNal-sense comprising BamH I)
is:
                                    (SEQ ID NO: 3)
5'-GACAGCAAATGGGTCGCGGATCCATGGCTTCCGCAACTTTCACC
G-3'

A downstream primer (CgNal-anti comprising Hind
III) is:
                                    (SEQ ID NO: 4)
5'-TGCTCGAGTGCGGCCGCAAGCTTTTAAGCGGTGTACAGGAATTCAT
C-3'
```

All the primers were synthesized by Suzhou GENEWIZ Corporation.

PCR Conditions for Gene:

Cycle 30 times according to the following parameters: denaturation at 98° C. for 10 seconds, annealing and extension at 68° C. for 1 minute, finally extension at 72° C. for 10 minutes.

Figure 1:
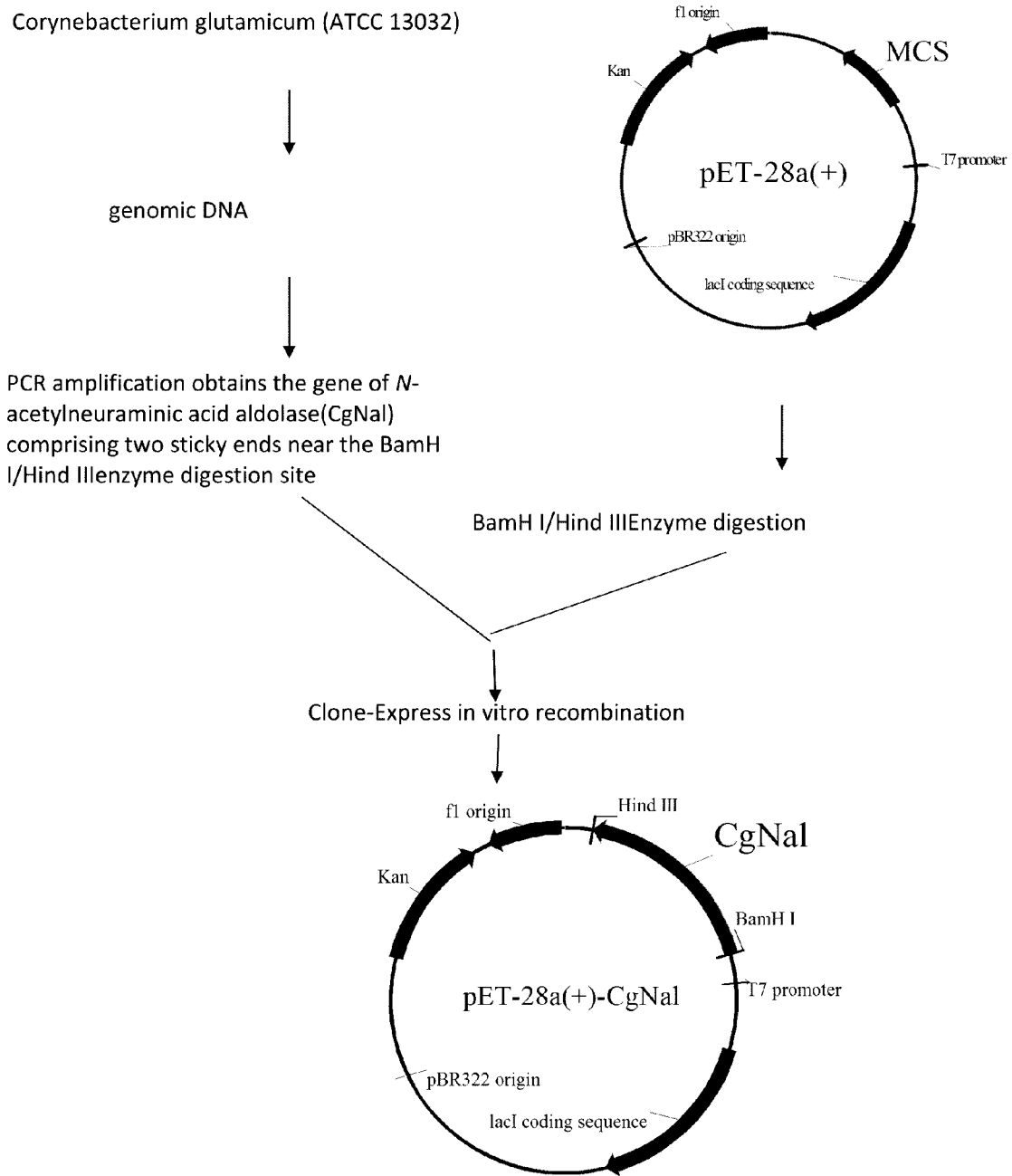
FIG. 1 is a graph of establishing the N-acetylneuraminic acid aldolase gene.

2. Transforming the Recombinant *E. coli* Rosseta (DE3):

The pET-28a vector (pET-28a, purchased from Novagen (Merck China)) was digested by BamH I and Hind III respectively, after conforming that the vectors were completely linearized, the target fragment of PCR and the linearized expression vector were extracted respectively, then with one-step clone kit (ClonExpress), 10 μL of linking product pET-28a-CgNal was added into 100 μL of Rosetta (DE3) competent cells, and placed on ice for 30 minutes, heat shocked at 42° C. for 90 seconds, placed on ice for 5 minutes. A pre-heated 0.9 mL of LB medium was added. Centrifuged at 200 rpm at 37° C. for 1 hour. A 200 μL of bacteria solution was added onto a LB plate containing 100 μg/mL kanamycin and chloramphenicol respectively, incubated at 37° C. overnight for 12 to 16 hours. The graph of establishment is seen in FIG. 1.

Example 2

Obtaining the Aldolase CgNal

1. Expression of N-Acetylneuraminic Acid Aldolase CgNal.

The recombinant strain *E. coli* Rosseta (pET-28a-CgNal) was picked up into a LB liquid medium containing antibiotics, incubated under vibration at 37° C. overnight. Then, inoculated to a fresh culture solution in a 1 (v/v) % inoculation amount, when incubated to $OD_{600}$ of about 0.6 at 37° C., IPTG was added to a final concentration of 0.2 $mmol·L^{-1}$, centrifuged at 200 rpm at 30° C., induced expression for 10 hours, then centrifuged (4° C., 10000 rpm, 10 minutes).

2. Purifying N-Acetylneuraminic Acid Aldolase CgNal.

The collected bacterial sludge was re-suspended in a 100 $mmol·L^{-1}$ Tris-HCl (PH 7.5) buffer, and the cells were ultrasonically lysed (power 300 W, sonicated for 3 seconds, interrupted for 5 seconds, totally 5 minutes), centrifuged (4° C., 12000 rpm, 15 minutes), and supernatant was removed.

Figure 2:
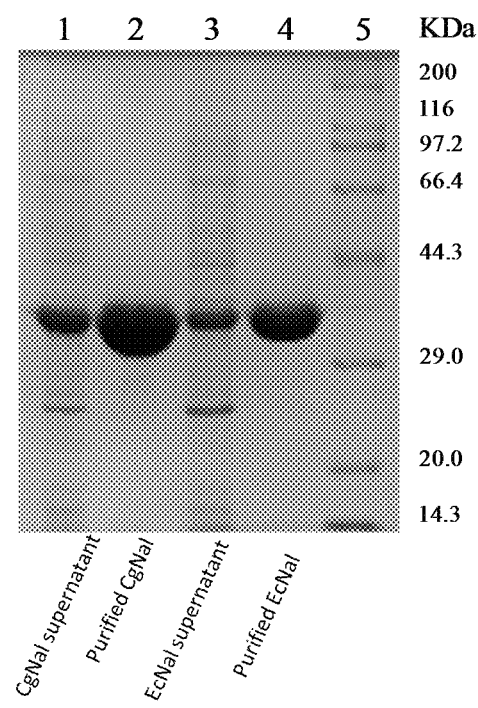
FIG. 2 is a graph of a sodium dodecyl sulfate polyacrylamide gel electrophoresis (SDS-PAGE) after expression of CgNal (from *Corynebacterium glutamicum* ATCC13032) and EcNal (from *Escherichia coli*). Wherein, 1 is CgNal crude enzyme, 2 is CgNal pure enzyme, 3 is EcNal crude enzyme, 4 is EcNal pure enzyme, and 5 is Marker.

The collected enzyme supernatant was added to a Ni-NTA column (Ni-NTA His Bind Resin, Novagen), and incubated on ice for 30 minutes. After the supernatant flowed through the column, the mixed protein was washed away with a 100 $mmol·L^{-1}$ Tris-HCl (pH 7.5) containing 20 $mmol·L^{-1}$ imidazole. Then, the target protein CgNal was eluted down with a 100 $mmol·L^{-1}$ Tris-HCl (pH 7.5) containing 500 $mmol·L^{-1}$ imidazole. Use aldolase EcNal from *Escherichia coli* as a control, and the purity and expression level of CgNal were detected by SDS-PAGE, which was shown in FIG. 2. The protein concentration of the purified CgNal was determined by Bradford method.

Example 3

Study on the Enzymatic Properties of the Aldolase CgNal

1. Detecting Method for CgNal Enzyme Activities

The enzyme activities of CgNal were divided into the enzyme activity of Neu5Ac synthesis reaction and the enzyme activity of Neu5Ac decomposition reaction. The enzyme activity on Neu5Ac synthesis reaction was defined as the enzyme amount required for synthesizing 1 μmol Neu5Ac per minute, and the enzyme activity on Neu5Ac decomposition reaction was defined as the enzyme amount required for decomposing 1 µmol Neu5Ac per minute, the enzyme activity detection solution for Neu5Ac decomposition reaction was 0.1 M pyruvic acid, 0.1 mol·L$^{-1}$ ManNAc and 0.1 mol·L$^{-1}$ Tris-HCl (pH 7.5 or 8.5); the enzyme activity detection solution for Neu5Ac decomposition reaction was 100 mmol·L$^{-1}$ Neu5Ac and 0.1 mol·L$^{-1}$ Tris-HCl (pH 7.5 or 8.5). The purified Nal was added into 1 ml of enzyme activity detection solution to the final concentration of 30 µg/ml (about 0.36 U/ml). After reaction at 37° C. for 20 minutes, the tube was heated in a boiling water for 5 minutes to stop the reaction, centrifuged at 12000 g for 10 minutes, and the sample was filtered with a 0.22 µm filter.

The substrate and the product were detected with Bio-Rad Aminex 87-H column by using Agilent 1200 HPLC,(5 mmol·L$^{-1}$ H2SO4 as a mobile phase, flow rate 0.6 ml/min, differential refractive index detector).

2. The Enzyme Activities of CgNal at Different pH Values.

Figure 3:
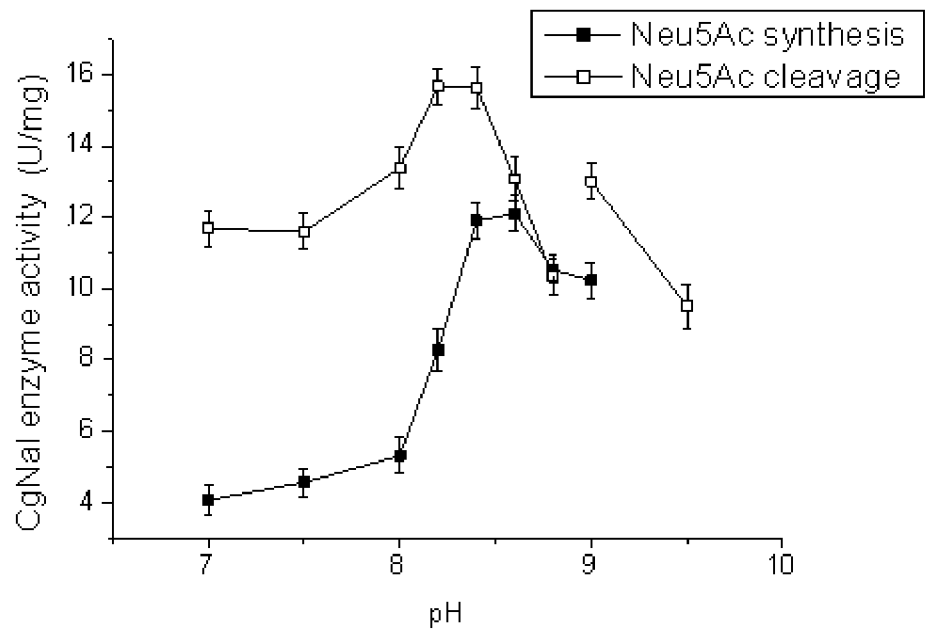
FIG. 3 is effect of pH on CgNal enzyme activity.

The following buffer was used in effect of pH on CgNal: 0.1 M Tris-HCl (pH 7 to 8.8) and 0.1 M glycine-NaOH buffer (pH 9.0 to 9.5). The enzyme activity was detected in the enzyme activity detection solutions of different pHs, in order to detect the effect of pH on the enzyme activity. The detection results showed that the activity of CgNal on Neu5Ac decomposition reaction between pH 7.5 and 8.4 was much higher than the activity on Neu5Ac synthesis reaction; when the pH was between 8.6 and 8.8, the decomposition activity of Neu5Ac was close to Neu5Ac synthesis activity (FIG. 3).

3. Effect of the Temperature on the CgNal

Figure 4:
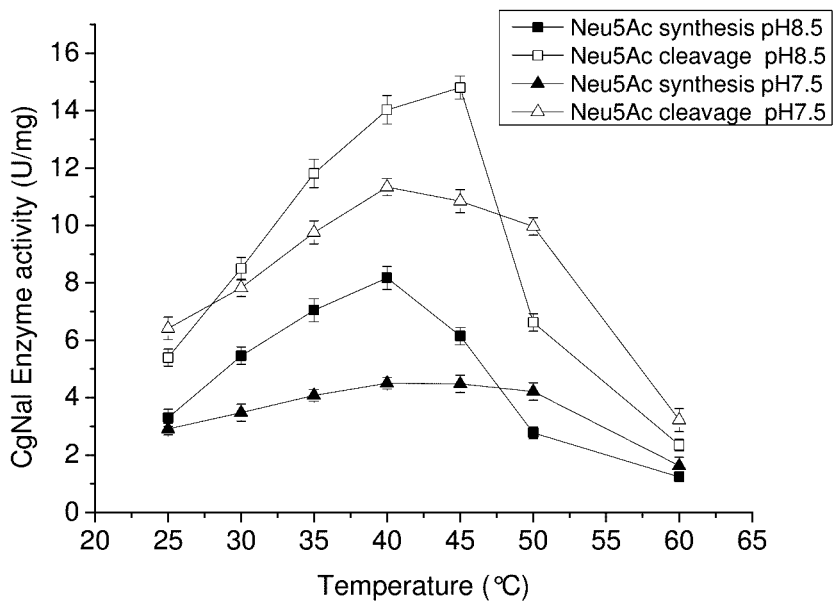
FIG. 4 is effect of temperature on CgNal enzyme activity.
Figure 5:
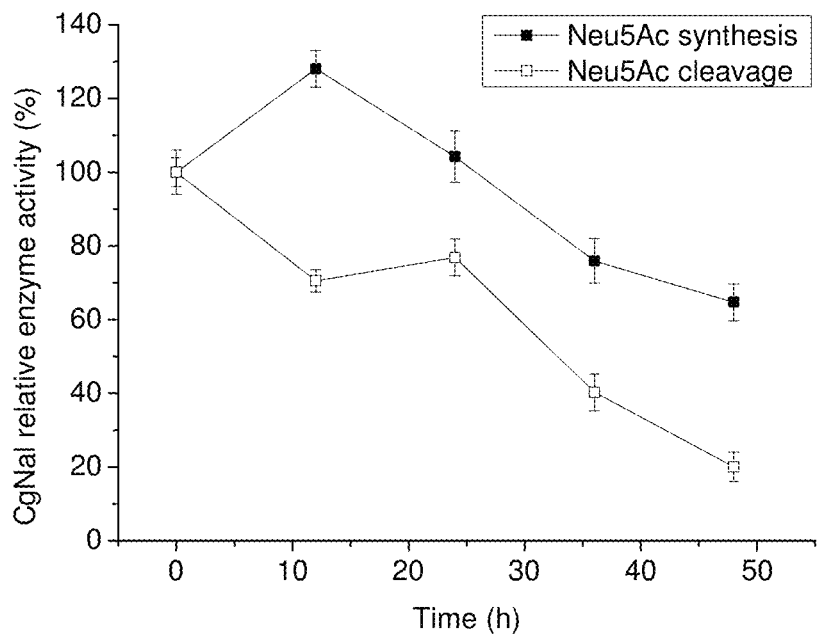
FIG. 5 is change of the enzyme activity of CgNal during the warm water bath.

The enzyme activities of both directions of the aldolase CgNal were detected by using a temperature gradient at pH 7.5 (25° C. to 60° C.), in order to find the optimum reaction temperature. At pH 7.5, the optimum temperature for CgNal was 40° C., the optimum temperature for decomposition and synthesis reaction of Neu5Ac were identical. At pH 8.5, the optimum temperature of Neu5Ac synthesis direction was 40° C., and the optimum temperature of Neu5Ac decomposition direction was 45° C. (FIG. 4). The CgNal was suspended in a 0.1 M Tris-HCl (pH 8.5) buffer, then placed in a warm water bath at 37° C. for 48 hours, and the change of enzyme activities was detected during the warm water bath, in order to determine the stability of CgNal. Within 10 hours prior to the warm water bath, Neu5Ac synthesis activity of CgNal showed a rising trend, after 36 hours of warm water bath it can still maintain about 80% of starting activity (FIG. 5).

4. Effects of Metal Ions and Surfactant on the CgNal Activity

Figure 6:
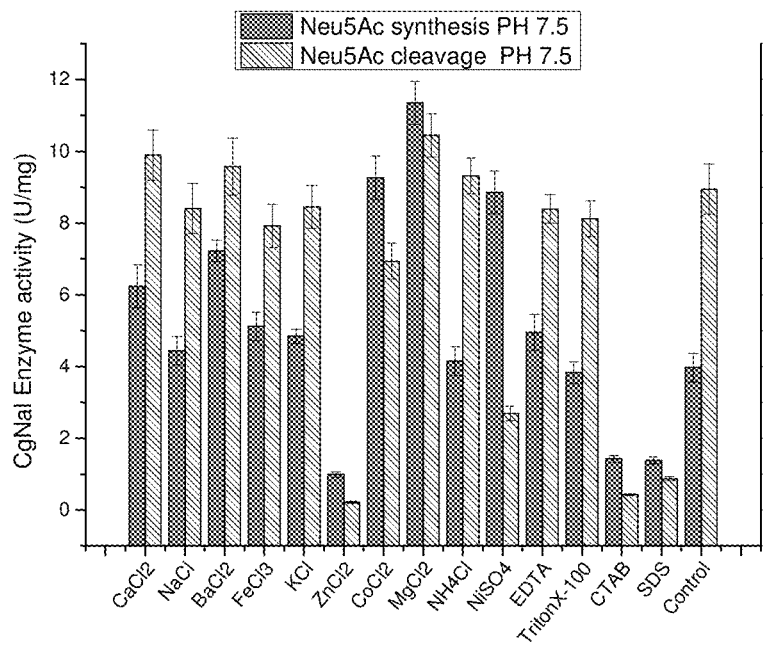
FIG. 6 is effects of metal ion and surfactant at pH 7.5 on CgNal enzyme activity
Figure 7:
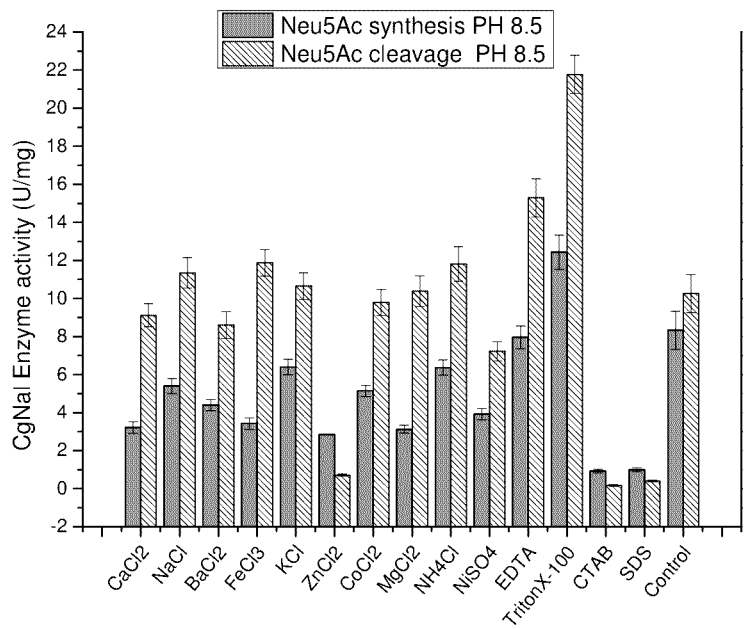
FIG. 7 is effects of metal ion and surfactant at pH 8.5 on CgNal enzyme activity.

To an enzyme activity detection solution of CgNal, 5 mM of CaCl$_2$, NaCl, BaCl$_2$, FeCl$_3$, KCl, ZnCl$_2$, CoCl$_2$, MgCl$_2$, NH$_4$Cl, NiSO$_4$, EDTA, CTAB and SDS were added, and a sample without adding any metal ion and surfactant was used as a control. The enzyme activities of CgNal at both pH 7.5 and pH 8.5 were detected. The enzyme activity of CgNal at pH 8.5 was much higher than the enzyme activity of CgNal at pH 7.5, and the effects of metal ions on CgNal under different pH conditions were quite different. At pH 7.5, ZnCl$_2$, CoCl$_2$, NiSO$_4$, CTAB and SDS all promoted reaction of CgNal in the synthesizing Neu5Ac direction, meanwhile they also inhibited the reaction in the decomposing Neu5Ac direction (FIG. 6). Whereas the metal ions at pH 8.5 had no significant activation effect on CgNal. ZnCl$_2$, CTAB and SDS promoted the superiority of Neu5Ac synthesis over Neu5Ac decomposition, but overall decreased the enzyme activity (FIG. 7). Therefore, at suitable pH value and under effect of metal ions and surfactant, the rate of CgNal in Neu5Ac synthesis direction was greater than the rate in Neu5Ac decomposition direction.

5. Determining the Enzyme Reaction Kinetic Constants for CgNal

The enzymatic reaction kinetic constants of CgNal at pH 7.5 and pH 8.5 on the substrates ManNAc, Neu5Ac and pyruvic acid were determined at different concentration of substrates. When the kinetic constant on pyruvic acid was determined, the fixed ManNAc concentration was 100 mM, and the pyruvic acid concentration varied between 1 and 100 mM. When the kinetic constant on ManNAc was determined, the fixed pyruvic acid concentration was 100 mM, and the concentration of ManNAc varied between 1 and 400 mM. When the kinetic constant on Neu5Ac was determined, the concentration of Neu5Ac varied between 1 and 200 mM. The kinetic constants of CgNal on Neu5Ac, ManNAc and pyruvic acid at pH 7.5 and pH 8.5 were as shown in Table 1. When the pH value was increased from 7.5 to 8.5, the Km and Vmax values of the substrate were greatly increased.

TABLE 1

| | Kinetic constants of CgNal | | | | | |
|---|---|---|---|---|---|---|
| | Neu5Ac | | ManNAc | | pyruvic acid | |
| pH | Km (mM) | Vmax (U/mg) | Km (mM) | Vmax (U/mg) | Km (mM) | Vmax (U/mg) |
| 7.5 | 33.5 | 16.74 | 53.3 | 10.2 | 14.7 | 10.98 |
| 8.5 | 87.7 | 79.6 | 92.1 | 73.2 | 72.4 | 76.64 |

Example 4

Catalytic Synthesis of Neu5Ac by Using CgNal as the Catalyst

Figure 8:
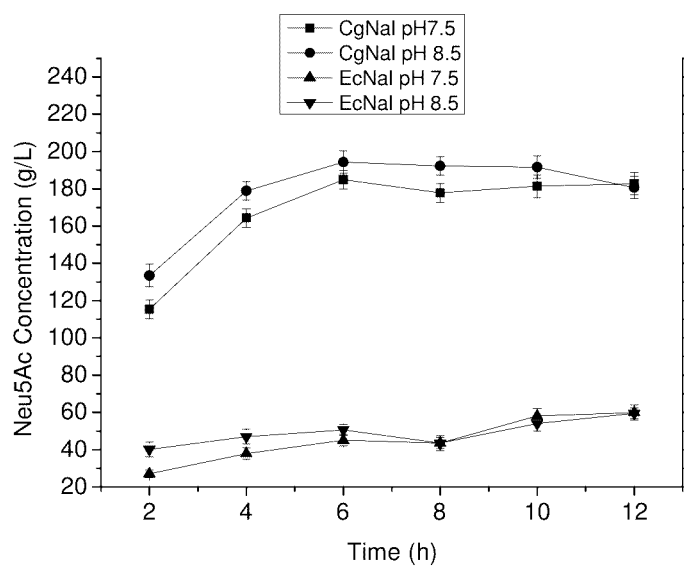
FIG. 8 is change of product concentration during synthesis of Neu5Ac using CgNal as the catalyst.

In a 20 ml of reaction system, the reaction solution was 50 mM Tris-HCl (pH 7.5 and pH 8.5) comprising 0.8 mol·L$^{-1}$ ManNAc and 2 mol·L$^{-1}$ pyruvic acid. Under the same conditions, 1 mL of inducer purified CgNal (180 U/mL) and EcNal (64 U/mL) were respectively added into the reaction solution. The catalytic condition was 37° C., 200 rpm for 12 hours. pH was respectively maintain to 7.5 and 8.5, During the reaction, the solution was sampled and the contents of ManNAc, pyruvic acid and Neu5Ac were detected. The catalysis results showed that the yield of CgNal was much higher than the yield of ECNal, and CgNal synthesized the highest amount of 185 g/L Neu5Ac within 12 hours. Within 6 hours prior to catalysis, the yield at pH 8.5 were significantly higher than the yield at pH 7.5, then in terms of catalysis results of EcNal and CgNal, the yield at pH 8.5 was very close to the yield at pH 7.5 (FIG. 8).

REFERENCES

1. Oriquat, G. A., et al., *Soluble CD14, sialic acid and L-Fucose in breast milk and their role in increasing the immunity of breast-fed infants*. American Journal of Biochemistry and Biotechnology, 2011. 7(Compendex): p. 21-28.
2. Tao, F., et al., *Biotechnological production and applications of N-acetyl-D-neuraminic acid: current state and perspectives*. Appl Microbiol Biotechnol, 2010. 87(4): p. 1281-9.

3. Xu, X., et al., *Production of N-acetyl-D-neuraminic acid by use of an efficient spore surface display system.* Applied and Environmental Microbiology, 2011. 77(Compendex): p. 3197-3201.
4. Hu, S., et al., *Coupled bioconversion for preparation of N-acetyl-D-neuraminic acid using immobilized N-acetyl-D-glucosamine-2-epimerase and N-acetyl-D-neuraminic acid lyase.* Appl Microbiol Biotechnol, 2010. 85(5): p. 1383-91.
5. Tabata, K., et al., *Production of N-acetyl—neuraminic acid by coupling bacteria expressing N-acetyl—glucosamine 2-epimerase and N-acetyl—neuraminic acid synthetase.* Enzyme and Microbial Technology, 2002. 30(3): p. 327-333.
6. North, R. A., et al., *Cloning, expression, purification, crystallization and preliminary X-ray diffraction studies of N-acetylneuraminic lyase from methicillin-resistant Staphylococcus aureus.* Acta Crystallographica Section F, 2013. 69(3): p. 306-312.
7. Sanchez-Carron, G., et al., *Molecular characterization of a novel N-acetylneuraminate lyase from Lactobacillus plantarum WCFS1.* Applied and Environmental Microbiology, 2011. 77(Compendex): p. 2471-2478.
8. Garcia Garcia, M. I., et al., *Characterization of a Novel N-Acetylneuraminate Lyase from Staphylococcus carnosus TM300 and Its Application to N-Acetylneuraminic Acid Production.* Journal of Agricultural and Food Chemistry, 2012. 60(30): p. 7450-7456.
9. Ishikawa, M. and S. Koizumi, *Microbial production of N-acetylneuraminic acid by genetically engineered Escherichia coli.* Carbohydrate Research, 2010. 345 (Compendex): p. 2605-2609.
10. Yamamoto, K., et al., *Serratia liquefaciens as a New Host Superior for Overproduction and Purification Using the N-Acetylneuraminate Lyase Gene of Escherichia coli.* Analytical Biochemistry, 1997. 246(2): p. 171-175.
11. Kruger, D., R. Schauer, and C. Traving, *Characterization and mutagenesis of the recombinant N-acetylneuraminate lyase from Clostridium perfringens.* European Journal of Biochemistry, 2001. 268(13): p. 3831-3839.
12. Uchida, Y., Y. Tsukada, and T. Sugimori, *Purification and properties of N-acetylneuraminate lyase from Escherichia coli.* J Biochem, 1984. 96(2): p. 507-22.
13. Schauer, R. and M. Wember, *Isolation and characterization of sialate lyase from pig kidney.* Biol Chem Hoppe Seyler, 1996. 377(5): p. 293-9.
14. Li, Y., et al., *Pasteurella multocida sialic acid aldolase: A promising biocatalyst.* Applied Microbiology and Biotechnology, 2008. 79(Compendex): p. 963-970.
15. Zahoor ul Hassan, A., S. Lindner, and V. F. Wendisch, *Metabolic engineering of Corynebacterium glutamicum aimed at alternative carbon sources and new products.*
16. Sun, W., et al., *Construction and expression of a polycistronic plasmid encoding N-acetylglucosamine 2-epimerase and N-acetylneuraminic acid lyase simultaneously for production of N-acetylneuraminic acid.* Bioresource Technology, 2013. 130(0): p. 23-29.

What is claimed is:

1. A method for using *Corynebacterium* N-acetylneuraminic acid aldolase for preparing N-acetylneuraminic acid with N-acetylmannosamine and pyruvic acid in a buffer.

2. The method according to claim 1, wherein the concentration of N-acetylneuraminic acid aldolase is from 0.36 to 300 U·mL$^{-1}$, the concentration of N-acetylmannosamine is from 100 to 1000 mmol·L$^{-1}$ and the concentration of pyruvic acid is from 100 to 2000 mmol·L$^{-1}$; a reaction temperature is between 25 and 60° C.; and a reaction time is between 0.1 and 12 hours.

3. The method according to claim 1, wherein the buffer is a Tris-HCl buffer at pH between 7 and 8.8, or a glycine-NaOH buffer at pH between 9.0 and 9.5.

4. The method according to claim 1, wherein the N-acetylneuraminic acid aldolase is produced by *E. coli* that is transformed by an expression vector that contains N-acetylneuraminic acid aldolase cDNA having the nucleic acid sequence as shown in SEQ ID NO: 1.

5. The method according to claim 4, the expression vector is a pET-28a vector.

* * * * *

SEQUENCE LISTING

```
<160> NUMBER OF SEQ ID NOS: 4

<210> SEQ ID NO 1
<211> LENGTH: 939
<212> TYPE: DNA
<213> ORGANISM: Corynebacterium glutamicum

<400> SEQUENCE: 1
atggcttccg caactttcac cggcgtgatc ccacccgtaa tgaccccact ccacgccgac      60
ggcagtgtgg atgtagaaag cctccgcaag ctcgttgacc acctcatcaa tggtggcgtc     120
gacggacttt tcgcactggg ctcctcaggc gaagcggcat tcctcacccg cgcccagcgc     180
aaactcgcac tgaccaccat catcgagcac accgcaggcc gcgttcccgt aactgctggt     240
gtcattgaaa ccaccactgc tcgcgtgatt gagctcgtgg aagatgccct ggaggctggt     300
gccgaaggcc tcgttgccac tgcacctttc tacacccgca cccacgatgt ggaaattgaa     360
gaacacttcc gcaagatcca cgccgccgct ccagagcttc cactgtttgc ctacaacatc     420
ccagtgtcgg tgcactccaa cctcaaccca gtcatgcttt tgacgctggc caaggatggc     480
gttcttgcag gcaccaagga ttccagtggc aatgatggcg caatccgctc actgatcgaa     540
gctcgtgatg atgctggact cactgagcag ttcaagatcc tcaccggcag cgaaaccacc     600
gttgatttcg cctaccttgc gggtgccgat ggagttgtcc caggcctggg caatgttgat     660
cctgcagcat acgcagcttt agcaaaactc tgcctcgatg gaaagtgggc agaagctgct     720
gctttgcaga agcgcatcaa ccacctcttc cacatcgtct tcgtgggaga cacctcccat     780
atgtccggat ccagcgctgg tttgggcggt ttcaagacag cactcgcaca ccttggcatt     840
attgaatcca atgcgatggc agttcctcac cagagcctca gcgacgaaga aactgctcgc     900
attcacgcca ttgttgatga attcctgtac accgcttaa                           939
```

<210> SEQ ID NO 2
<211> LENGTH: 312
<212> TYPE: PRT
<213> ORGANISM: Corynebacterium glutamicum

<400> SEQUENCE: 2

Met Ala Ser Ala Thr Phe Thr Gly Val Ile Pro Val Met Thr Pro
1               5                   10                  15

Leu His Ala Asp Gly Ser Val Asp Val Glu Ser Leu Arg Lys Leu Val
                20                  25                  30

Asp His Leu Ile Asn Gly Gly Val Asp Gly Leu Phe Ala Leu Gly Ser
                35                  40                  45

Ser Gly Glu Ala Ala Phe Leu Thr Arg Ala Gln Arg Lys Leu Ala Leu
    50                  55                  60

Thr Thr Ile Ile Glu His Thr Ala Gly Arg Val Pro Val Thr Ala Gly
65                  70                  75                  80

Val Ile Glu Thr Thr Thr Ala Arg Val Ile Glu Leu Val Glu Asp Ala
                85                  90                  95

Leu Glu Ala Gly Ala Glu Gly Leu Val Ala Thr Ala Pro Phe Tyr Thr
                100                 105                 110

Arg Thr His Asp Val Glu Ile Glu Glu His Phe Arg Lys Ile His Ala
                115                 120                 125

Ala Ala Pro Glu Leu Pro Leu Phe Ala Tyr Asn Ile Pro Val Ser Val
        130                 135                 140

His Ser Asn Leu Asn Pro Val Met Leu Leu Thr Leu Ala Lys Asp Gly
145                 150                 155                 160

Val Leu Ala Gly Thr Lys Asp Ser Ser Gly Asn Asp Gly Ala Ile Arg
                165                 170                 175

Ser Leu Ile Glu Ala Arg Asp Asp Ala Gly Leu Thr Glu Gln Phe Lys
                180                 185                 190

Ile Leu Thr Gly Ser Glu Thr Thr Val Asp Phe Ala Tyr Leu Ala Gly
                195                 200                 205

Ala Asp Gly Val Val Pro Gly Leu Gly Asn Val Asp Pro Ala Ala Tyr
        210                 215                 220

Ala Ala Leu Ala Lys Leu Cys Leu Asp Gly Lys Trp Ala Glu Ala Ala
225                 230                 235                 240

Ala Leu Gln Lys Arg Ile Asn His Leu Phe His Ile Val Phe Val Gly
                245                 250                 255

Asp Thr Ser His Met Ser Gly Ser Ala Gly Leu Gly Gly Phe Lys
                260                 265                 270

Thr Ala Leu Ala His Leu Gly Ile Ile Glu Ser Asn Ala Met Ala Val
        275                 280                 285

Pro His Gln Ser Leu Ser Asp Glu Glu Thr Ala Arg Ile His Ala Ile
        290                 295                 300

Val Asp Glu Phe Leu Tyr Thr Ala
305                 310

<210> SEQ ID NO 3
<211> LENGTH: 45
<212> TYPE: DNA
<213> ORGANISM: Artificial Sequence
<220> FEATURE:
<223> OTHER INFORMATION: Primer for PCR

<400> SEQUENCE: 3
gacagcaaat gggtcgcgga tccatggctt ccgcaacttt caccg    45

```
<210> SEQ ID NO 4
<211> LENGTH: 47
<212> TYPE: DNA
<213> ORGANISM: Artificial Sequence
<220> FEATURE:
<223> OTHER INFORMATION: Primer for PCR

<400> SEQUENCE: 4
tgctcgagtg cggccgcaag cttttaagcg gtgtacagga attcatc                47
```